(12) United States Patent
Wong et al.

(10) Patent No.: US 7,602,284 B2
(45) Date of Patent: Oct. 13, 2009

(54) STERILIZER CASSETTE HANDLING SYSTEM WITH DATA LINK

(75) Inventors: William Wong, Encinitas, CA (US); Vishnu R. Raja, Irvine, CA (US); Alfredo M. Choperena, San Juan Capistrano, CA (US)

(73) Assignee: Ethicon, Inc., Somerville, NJ (US)

( * ) Notice: Subject to any disclaimer, the term of this patent is extended or adjusted under 35 U.S.C. 154(b) by 413 days.

(21) Appl. No.: 10/793,115

(22) Filed: Mar. 4, 2004

(65) Prior Publication Data

US 2005/0197737 A1    Sep. 8, 2005

(51) Int. Cl.
   *G08B 1/08* (2006.01)
(52) U.S. Cl. .............. 340/539.22; 340/539.32; 340/572.1; 340/568.1
(58) Field of Classification Search ........... 340/539.22, 340/539.32, 572.1, 568.1, 10.3, 825.36, 825.49
   See application file for complete search history.

(56) References Cited

U.S. PATENT DOCUMENTS

| | | |
|---|---|---|
| 4,442,507 A | 4/1984 | Roesner |
| 4,796,074 A | 1/1989 | Roesner |
| 4,817,800 A | 4/1989 | Williams et al. |
| 4,869,286 A | 9/1989 | Williams et al. |
| 4,899,519 A | 2/1990 | Williams et al. |
| 4,909,287 A | 3/1990 | Williams et al. |
| 4,913,196 A | 4/1990 | Williams et al. |
| 4,938,262 A | 7/1990 | Williams et al. |
| 4,941,518 A | 7/1990 | Williams et al. |
| 5,095,362 A | 3/1992 | Roesner |
| 5,296,722 A | 3/1994 | Potash et al. |
| 5,347,280 A | 9/1994 | Schuermann |
| 5,378,880 A | 1/1995 | Eberhardt |
| 5,407,851 A | 4/1995 | Roesner |
| 5,521,601 A | 5/1996 | Kandlur et al. |
| 5,528,222 A | 6/1996 | Moskowitz et al. |
| 5,541,604 A | 7/1996 | Meier |
| 5,550,547 A | 8/1996 | Chan et al. |
| 5,565,846 A | 10/1996 | Geiszler et al. |
| 5,625,341 A | 4/1997 | Giles et al. |
| 5,682,143 A | 10/1997 | Brady et al. |

(Continued)

FOREIGN PATENT DOCUMENTS

EP      0 822 457 A      12/1998

(Continued)

OTHER PUBLICATIONS

Jan. 2004 Contents Features, Scientific American, vol. 290, No. 1 "RFID A Key to Automating Everything", Roby Want, pp. 56-65.

(Continued)

*Primary Examiner*—Daryl Pope

(57) ABSTRACT

A cassette handling system for sterilant filled cassettes employs RFID or other electromagnetic signal technology to track the cassettes. A method for tracking the sterilant cassettes includes the steps of reading for the presence of a cassette within a cassette processing area of the sterilizer by transmitting a non-optical electromagnetic signal between the cassette and a receiver on the sterilizer, via the electromagnetic signal transmitting identifying information between the cassette and the receiver, and verifying that a proper cassette is loaded into the sterilizer based upon the identifying information.

22 Claims, 18 Drawing Sheets

U.S. PATENT DOCUMENTS

| | | | |
|---|---|---|---|
| 5,842,325 A * | 12/1998 | Godly et al. ................... 53/411 |
| 5,882,611 A | 3/1999 | Williams et al. |
| 5,887,716 A | 3/1999 | Williams et al. |
| 6,412,340 B1 | 7/2002 | Nguyen et al. |
| 6,600,418 B2 | 7/2003 | Francis et al. |
| 6,600,420 B2 | 7/2003 | Goff et al. |
| 6,714,121 B1 * | 3/2004 | Moore ........................ 340/10.3 |
| 6,729,369 B2 * | 5/2004 | Neas et al. .................. 141/231 |
| 6,771,369 B2 * | 8/2004 | Rzasa et al. ................. 356/326 |
| 6,956,538 B2 * | 10/2005 | Moore ........................ 343/878 |
| 7,006,894 B2 * | 2/2006 | de la Huerga ............... 700/244 |
| 7,070,053 B1 * | 7/2006 | Abrams et al. ........... 206/459.5 |
| 7,205,016 B2 * | 4/2007 | Garwood .................... 426/108 |
| 7,256,699 B2 * | 8/2007 | Tethrake et al. .......... 340/572.8 |
| 2002/0067267 A1 | 6/2002 | Kirkham |
| 2002/0130778 A1 | 9/2002 | Nicholson |
| 2002/0161460 A1 | 10/2002 | Noguchi |
| 2003/0072676 A1 | 4/2003 | Fletcher-Hayes et al. |

FOREIGN PATENT DOCUMENTS

| | | |
|---|---|---|
| EP | 0882457 B1 | 5/2004 |
| FR | 2 717 593 A | 9/1995 |

OTHER PUBLICATIONS

"Temperature Tracking", Identic Solutions, "Intelligent Long Range", Nov. 2003.
The AIM Global Netwrok, Standards, RFID Basics Primer, pp. 1-11, 1998/99.
European Search Report for EP 05 25 1284 dated Sep. 9, 2005.
Supplementary EP Search Report for EP Appl. No. 05251264.7 dated Jun. 29, 2005.
European Search Report for EP Application No. 05251264.7 dated Sep. 9, 2005 (5 pages).

* cited by examiner

STERILIZER CASSETTE HANDLING SYSTEM WITH DATA LINK

BACKGROUND OF THE INVENTION

This application relates to the delivery of sterilant from a cassette to an instrument sterilizer, and more particularly to the extraction of sterilant from the cassette.

One popular method for sterilizing instruments, such as medical devices, is to contact the devices with a vapor phase chemical sterilant, such as hydrogen peroxide. In many such sterilizers, it is preferred to deliver the sterilant in liquid form and vaporize it in the sterilizer. One particularly convenient and accurate method for delivering the liquid sterilant is to put a predetermined quantity of sterilant into a cassette and deliver the cassette to the sterilizer. The sterilizer then automatically extracts the sterilant from the cassette and uses it for sterilization procedure. Typically, such a cassette would entail multiple cells containing equal amounts of liquid sterilant with a sterilization procedure employing the sterilant from one or more cells. Such a system is currently available in the STERRAD® sterilization system available from Advanced Sterilization Products in Irvine, Calif.

U.S. Pat. Nos. 4,817,800; 4,869,286; 4,899,519; 4,909,287; 4,913,196; 4,938,262; 4,941,518; 5,882,611; 5,887,716; and 6,412,340, each incorporated herein by reference, disclose such cassettes and a method for draining liquid sterilant from a cell within a cassette.

If an operator employs a cassette which has already been used, time can be wasted before the operator realizes that no sterilant has reached the articles during the failed sterilization cycle. A convenient disposal method for spent cassettes would also be desirable.

The present invention overcomes these and other limitations of the prior art.

SUMMARY OF THE INVENTION

A method according to the present invention for tracking sterilant cassettes within a sterilizer includes the steps of: reading for the presence of a cassette within a cassette processing area of the sterilizer by transmitting a non-optical electromagnetic signal between the cassette and a receiver on the sterilizer; via the electromagnetic signal transmitting identifying information between the cassette and the receiver; and verifying that a proper cassette is loaded into the sterilizer based upon the identifying information.

The electromagnetic signal can comprise, for instance, a magnetic coupling between the receiver and the cassette, or an inductive coupling between the receiver and the cassette, or a conductive coupling between the receiver and the cassette, or a radio frequency transmission.

Preferably, the receiver comprises one or more antennas, preferably sequenced in use to identify the location of the cassette.

Preferably, the cassette contains an RFID tag.

The method preferably further includes the step of altering a portion of data stored in the RFID tag, such as filling status of sterilant in the cassette and the filling status data is updated when sterilant is removed from the cassette. Where the cassette contains multiple cells containing the sterilant preferably, the RFID tag includes a filling status of sterilant in each of the cells and the filling status data for a cell is updated when sterilant is removed from that cell. If less than the entire contents of one of the cells is removed, preferably this data is stored on the tag.

In one aspect of the invention, the RFID tag contains temperature sensing instrumentation and the data includes temperature information regarding the shipping and storage temperatures to which the cassette has been subjected.

In another aspect of the invention, the data is updated with one or more cycle parameters, such as a concentration of sterilant achieved during a cycle.

Updateable data can also include the amount of time the cassette has spent within the sterilizer. Identifying data can include the type of cycle for which a particular cell or group of cells is intended (such as cycle times, amount of sterilant to be used etc.). It could also include an expiration date for the cassette and the method further include the step of rejecting the cassette if the expiration date has passed.

Preferably, the method further includes the step of reading the presence and filling status of a spent cassette collection box via a non-optical electromagnetic signal.

A cassette, according to the present invention, comprises one or more cells having therein a liquid sterilant, and further comprises indicia readable electromagnetically and containing identifying data about the cassette including data identifying the liquid sterilant contents thereof.

The data can include such things as a filling status of the cells, an expiration date of the liquid sterilant, a manufacturing date of the cassette, a serial number of the cassette, a lot number of the cassette, and a maximum amount of time the cassette may reside within a sterilizer.

Preferably, the indicia comprises an RFID tag, more preferably an RFID tag with updateable memory. The updateable memory can contains such data as the filling status of the one or more cells within the cassette data regarding the cell being partially filled, temperature information regarding the shipping and storage temperatures to which the cassette has been subjected, one or more cycle parameters (such as a concentration of sterilant achieved during a cycle), and the amount of time the cassette has spent within a sterilizer.

A spent cassette collection box for receiving spent cassettes from a sterilizer, according to the present invention, comprises a bottom wall, upstanding walls attached to the bottom wall which extend upwards to terminate in an upper edge, and indicia readable electromagnetically and containing identifying data about the spent cassette collection box including data identifying its capacity to receive cassettes.

Preferably, the indicia is an RFID tag and more preferably, is an RFID tag having updateable data including a quantity of cassettes currently in the box.

DETAILED DESCRIPTION

Figure 1:
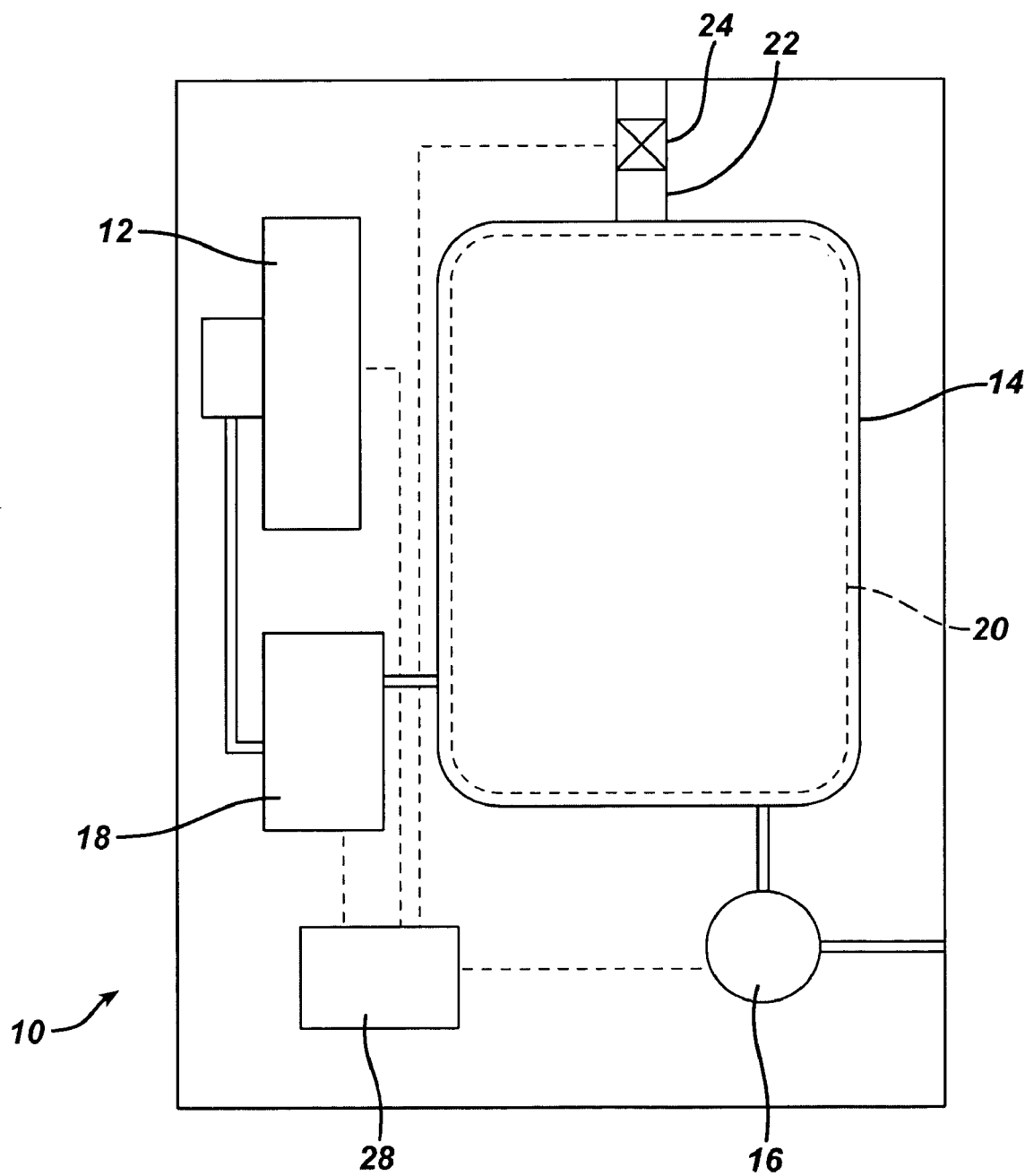
FIG. 1 is a block diagram of a sterilizer employing a cassette handling system according to the present invention.

FIG. 1 shows in block diagram form a vapor phase sterilizer 10 employing a cassette handling system 12 according to the present invention. The sterilizer 10 comprises a vacuum chamber 14 and a vacuum pump 16 for exhausting atmosphere therefrom. A vaporizer 18 receives liquid sterilant from the cassette handling system 12 and supplies it in vapor form to the vacuum chamber 14. A screen grid electrode 20 is provided within the vacuum chamber 14 for exciting the contents into the plasma phase during a portion of the sterilization cycle. A micro filtered vent 22 and valve 24 allow sterile air to enter the vacuum chamber 14 and break the vacuum therein. A control system 28 ties in to all of the major components, sensors and the like within the sterilizer 10 to control the sterilization cycle.

A typical sterilization cycle might include drawing a vacuum upon the vacuum chamber 14 and turning on power to the electrode 20 to evaporate and extract water from the vacuum chamber 14. The electrode 20 is then powered off and a low vacuum of less than 1 torr drawn on the vacuum chamber 14. Sterilant, such as hydrogen peroxide solution, is vaporized by the vaporizer 18 and introduced into the vacuum chamber 14 where it diffuses into contact with the items to be sterilized and kills microorganisms thereon. Near the end of the cycle, power is again applied to the electrode 20 and the sterilant is driven into the plasma phase. The electrodes 20 are powered down and filtered air is drawn in through the valve 24. This process can be repeated.

Figure 2:
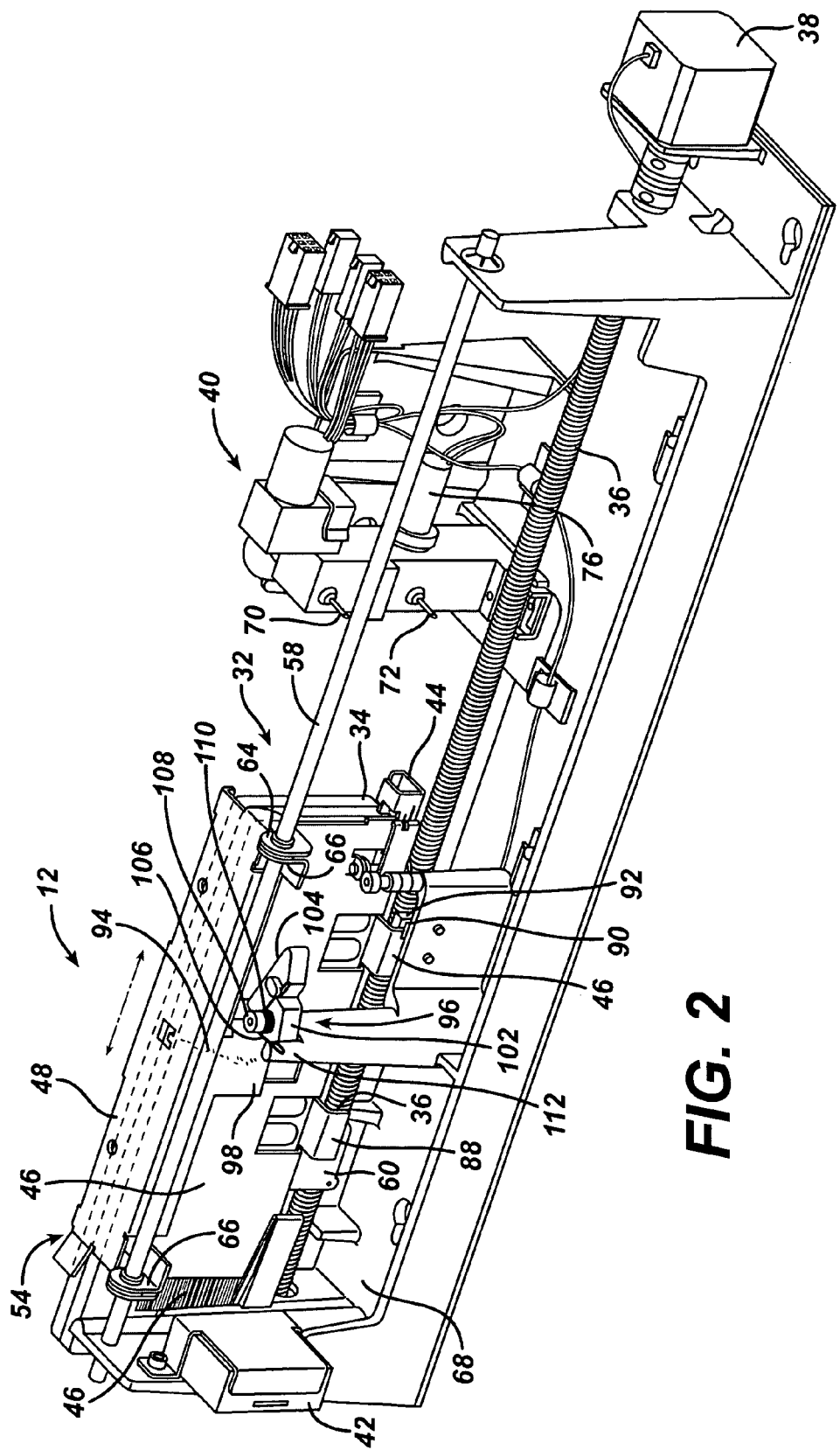
FIG. 2 is a rear perspective view of a cassette handling system according to the present invention.
Figure 3:
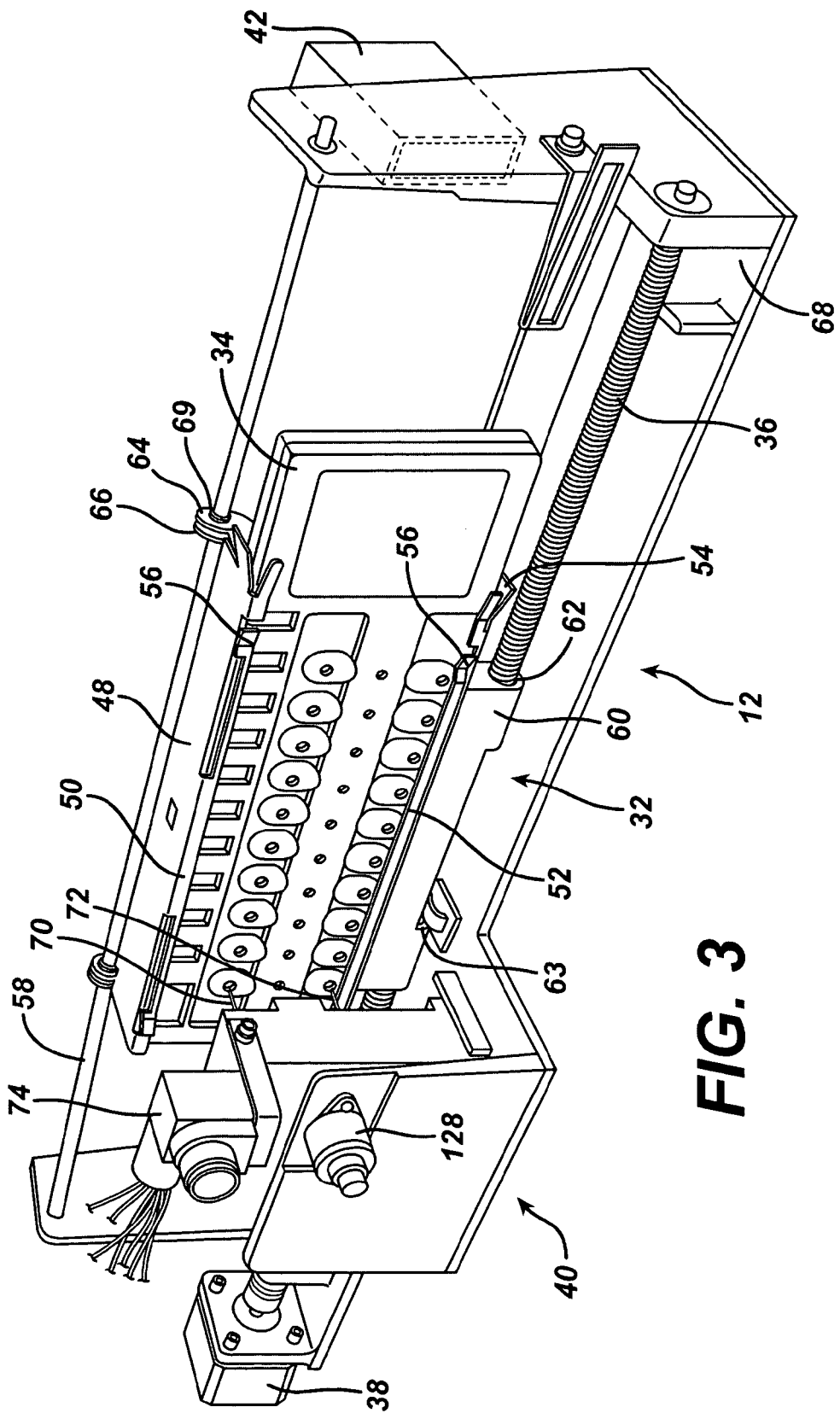
FIG. 3 is a front perspective view of the cassette handling system of FIG. 2.
Figure 4:
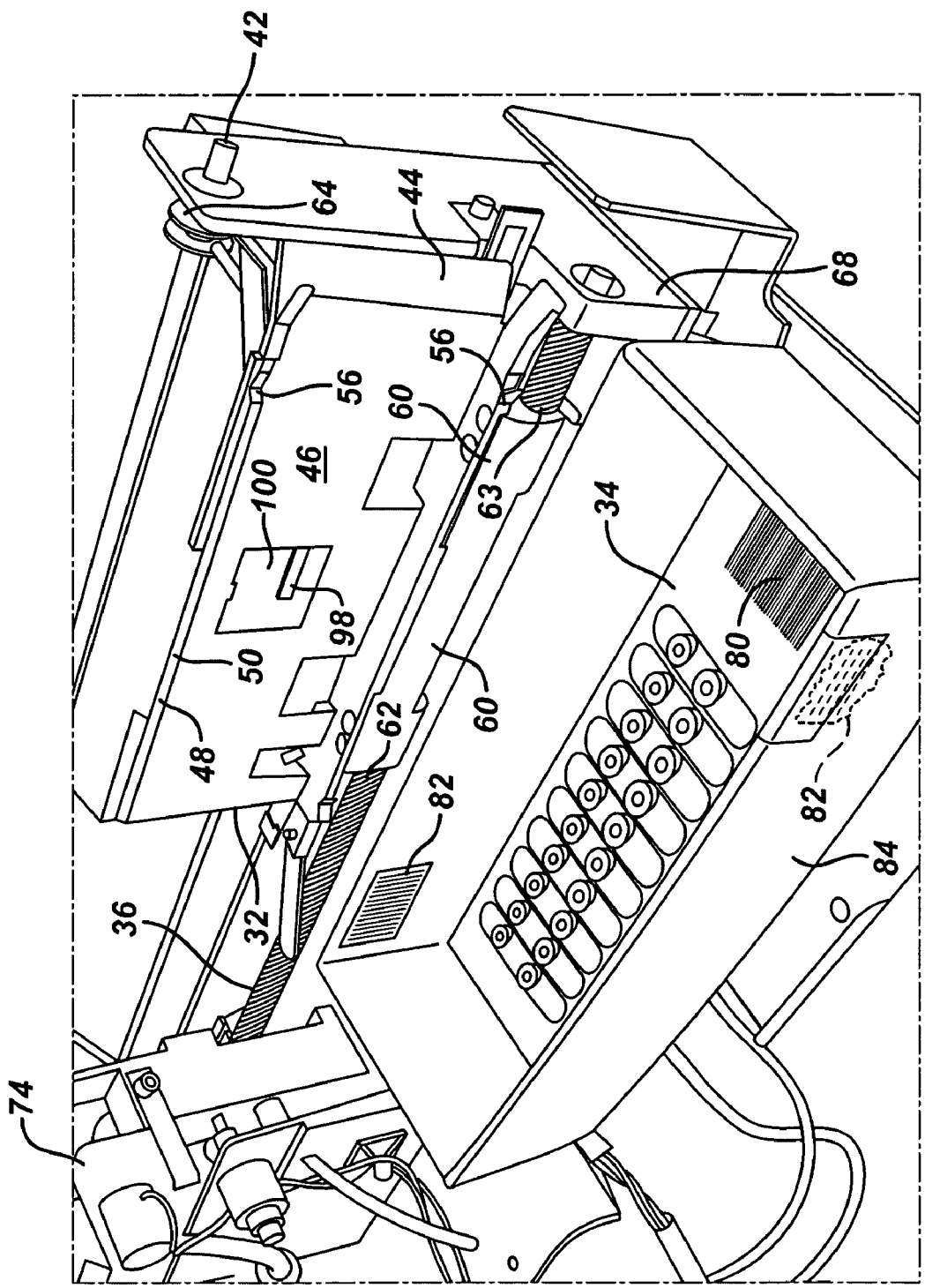
FIG. 4 is a front perspective view of the cassette handling system of FIG. 2 showing a spent cassette collection box.

Turning also to FIGS. 2 to 4, the cassette handling system 12 according to the present invention is shown. It comprises in gross, a carriage 32 for holding a cassette 34, a lead screw 36 and motor 38, an extractor subsystem 40 and a scanner 42.

The carriage 32 comprises a bottom panel 44, a side panel 46 and top panel 48 along with small vertical flanges 50 and 52 on the top and bottom panels 48 and 44, respectively, to capture the cassette 34. The bottom, side and top panels 44, 46 and 48 flare outwardly at an entrance 54 of the carriage to aid in insertion of the cassette 34. Two spring catches 56 on the flanges 50 and 52 engage irregular surfaces of the cassette 34 to firmly position the cassette 34 within the carriage 32.

The carriage 32 travels along the lead screw 36 and is supported on an upper rail 58. A lead screw nut 60 attached to the bottom panel 44 and having a threaded opening 62 and an unthreaded opening 63 receives the lead screw 36 and effects horizontal movement of the carriage 32 in response to rotations of the lead screw 36. Flanges 64 extend outwardly from the top panel 48 and flanges 66 extend outwardly from the side panel 46 each having openings 69 for receiving the upper rail 58. The motor 38 is preferable a stepping motor and connects to the lead screw 36 to precisely control the horizontal position of the cassette 34 relative to a frame 68.

The extraction assembly 40 comprises an upper needle 70 and a lower needle 72, each being of a lumened configuration. The upper needle connects to an air pump 74 which can force air out through the upper needle 70. The lower needle 72 connects to a valve 76 and from there is plumbed to the vaporizer 18.

The scanner 42 is oriented so as to be able to read a barcode 80 on the cassette 34 as well as a barcode 82 on a spent cassette collection box 84. Upon insertion of the cassette 34 into the carriage 32 the scanner 42 reads the cassette barcode 80. The barcode 80 is preferably encoded with information regarding the contents of the cassette 34, including lot numbers and expiration dates. This information can be used to determine whether the cassette 34 is fresh and of the correct type and whether the cassette 34 has been used in the system before and thus is at least partially empty. The code is communicated to the control system 28 which makes these determinations.

The scanner 42 can also see the spent cassette collection box barcode 82 when the carriage 32 moves inwardly and away from the scanner 42. Each spent cassette collection box 84 preferably has two barcodes 82, one in each opposing corner so that the scanner 42 can see one of them regardless of which end of the spent cassette collection box 84 is inserted first. With the spent cassette collection box 84 filled, the spent cassettes 34 block the barcode 82 which alerts the control system 28 that there is no capacity for receiving additional spent cassettes 34. Preferably this message will be output to a user, such as on a display screen (not shown). If the cassette 34 is empty it will not be ejected and no new cycles will be run until a spent cassette collection box 84 having capacity to receive a spent cassette 34 is placed into the sterilizer 10.

A forward flag 86 and rearward flag 88 project outwardly and downwardly from the carriage side panel 46. They slide through a slot 90 in a slot sensor 92 which detects their presence within the slot 90, such as by blocking a beam of light. Travel of the front flag 86 and rear flag 88 through the slot sensor 92 provides a reference location of the carriage 32 to the control system 28.

The top panel 48 of the carriage 32 can rotate about the upper rail 58. A spring 94 between the top panel 48 and side panel 46 biases the top panel 48 downwardly to hold the cassette 34 within the carriage 32. A disposing cam 96 sits behind the side panel 46 and aligns with an ejecting tab 98 which extends outwardly and downwardly from the top panel 48 and which can project through an opening 100 in the side panel 46 when the top panel 48 rotates upwardly. Such rotation of the top panel 48 releases its hold upon the cassette 34 and due to the ejecting tab 98 projecting through the opening 100 pushes the cassette 34 out of the carriage 32 and into the spent cassette collection box.

Figure 5:
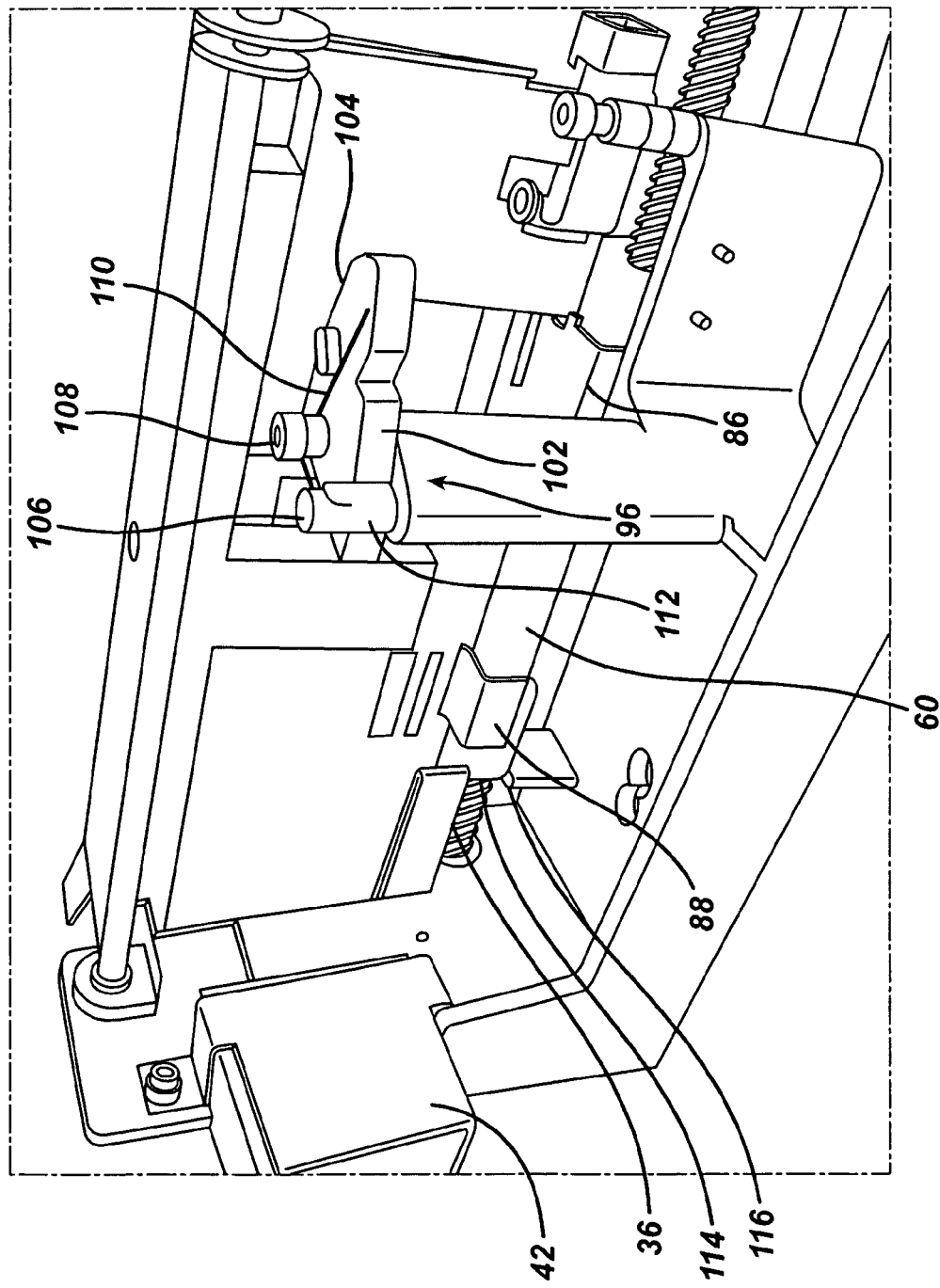
FIG. 5 is a rear perspective view of the cassette handling system of FIG. 2 showing its carriage in the insert position.

The disposing cam 96 controls rotation of the top panel 48. It comprises a generally triangular shape, having an outwardly facing side 102, forwardly facing side 104 and rearwardly facing side 106. Turning also now to FIG. 5, it mounts for rotation upon an upwardly extending spindle 108. A spring 110 biases the disposing cam 96 counterclockwise, urging the outwardly facing side 102 into contact with an abutment 112. Inward movements of the carriage 32 allow the ejecting tab 98 to cam over the rearwardly facing side 106 of the disposing cam 96, thus allowing the disposing cam 96 to rotate clockwise and allow the ejecting tab 98 to pass thereby without effecting rotation of the top panel 48. However, outward movement of the carriage 32 causes the ejecting tab 98 to cam over the forwardly facing side 104 of the disposing cam 96. During such motion contact between the outwardly facings side 102 of the disposing cam 96 and the abutment 112 prevents rotation of the disposing cam 96. The camming of the ejecting tab 98 thus causes it to move laterally toward the side panel 46 thereby rotating the top panel 48 upwardly and releasing the cassette 34 from the carriage 32.

Figure 6:
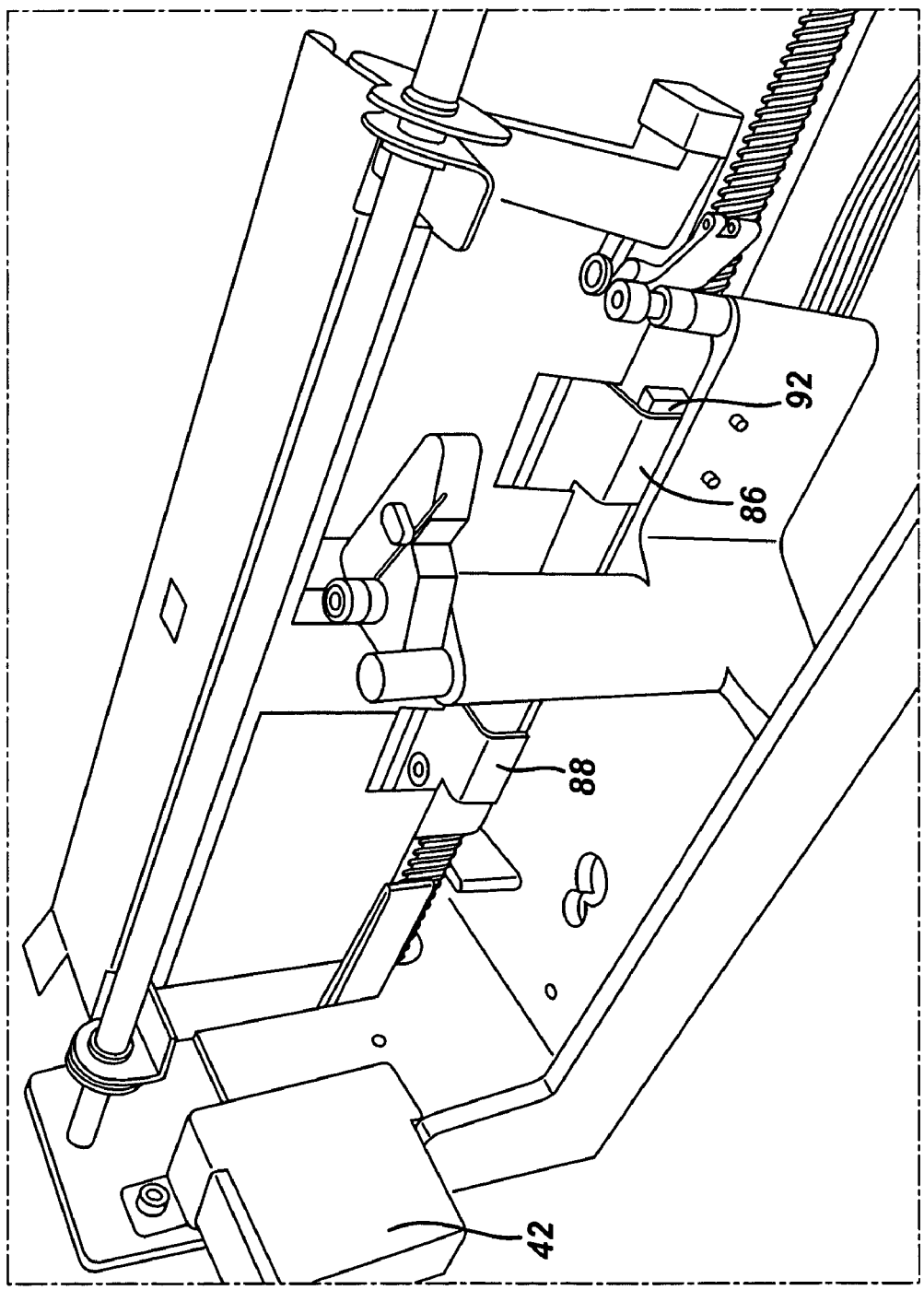
FIG. 6 is a rear perspective view of the cassette handling system of FIG. 2 showing its carriage as it moves toward the home position.

Prior to inserting the cassette 34 the carriage 32 is fully retracted to its outward position (to the left as shown in FIG. 5). In this position also, a forward end 114 on the lead screw nut 60 engages a stop 116 thus positively locating the position of the carriage 32. Turning also now to FIG. 6, manual insertion of the cassette 34 causes the carriage 32 to move inwardly (to the right as shown in FIG. 6) and moves the front flag 86 into the slot sensor 92. This movement is preferably caused by the physical force from inserting the cassette 34, however, a torque or other sensor could be applied to allow the stepping motor 38 to take over this movement upon feeling the force of the cassette 34 being inserted into the carriage 32. Allowing this movement to come from the force of the insertion of the cassette 34 ensures that the cassette 34 is fully seated within the carriage 32 before the movement begins.

Figure 7:
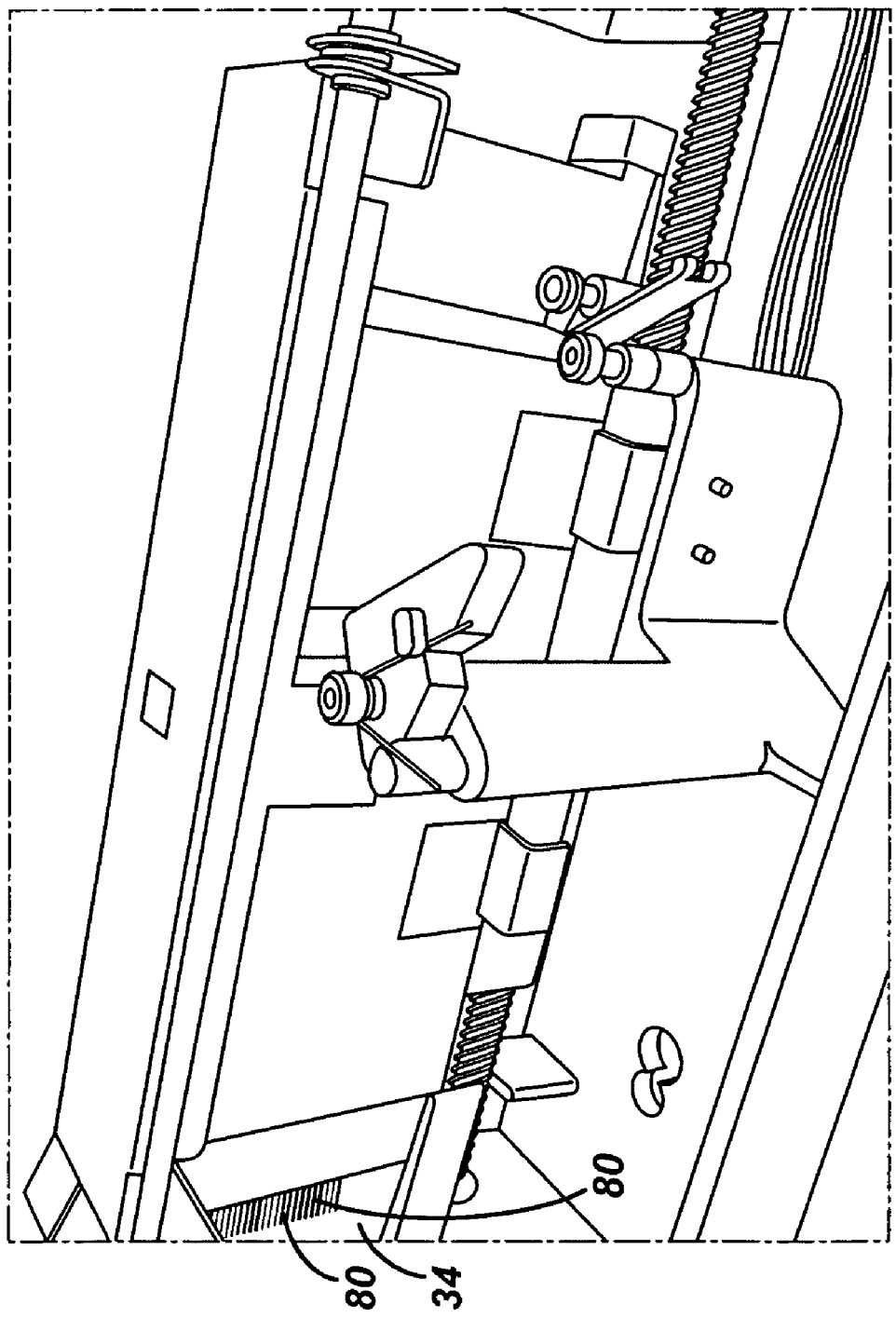
FIG. 7 is a rear perspective view of the cassette handling system of FIG. 2 showing its carriage in position to read a bar code on the cassette.

Once the front flag 86 is read by the slot sensor 92 the stepper motor 38 takes over and starts to move the carriage 32 inwardly. Turning also now to FIG. 7, during this stage, the scanner 42 scans the barcode 80 on the cassette 34. The control system 28 interprets the information coming from the barcode 80 and determines whether the cassette 34 has been used in the sterilizer 10 before, whether the cassette contains fresh sterilant, and other data as appropriate. Preferably, the information on the barcode 80 is encrypted to prevent unauthorized parties from creating cassettes which may not meet the quality standards necessary for proper sterilization.

If the control system 28 rejects the cassette 34 a carriage 32 is moved sufficiently inwardly so as to pass the ejecting tab 98 past the disposing cam 96 and is then moved back to the insertion position shown in FIG. 5 to eject the rejected cassette 34. If the cassette 34 is accepted, the carriage 32 continues inward movement to the home position as shown in FIG. 8 in which the rear flag 88 has just passed out of the slot sensor 92.

Figure 9:
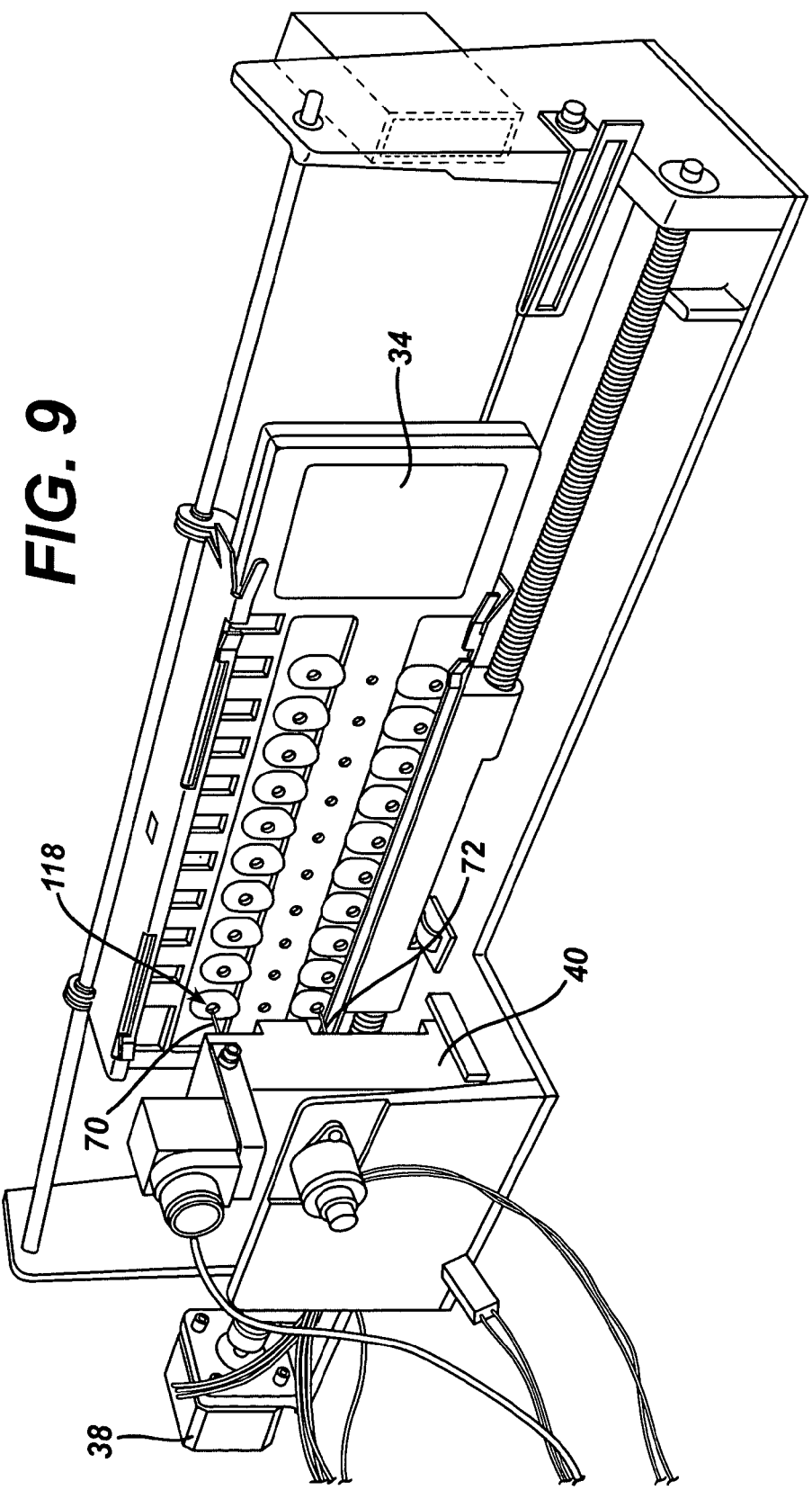
FIG. 9 is a front perspective view of the cassette handling system of FIG. 2 showing its carriage in position to tap the cassette's first cell.
Figure 10:
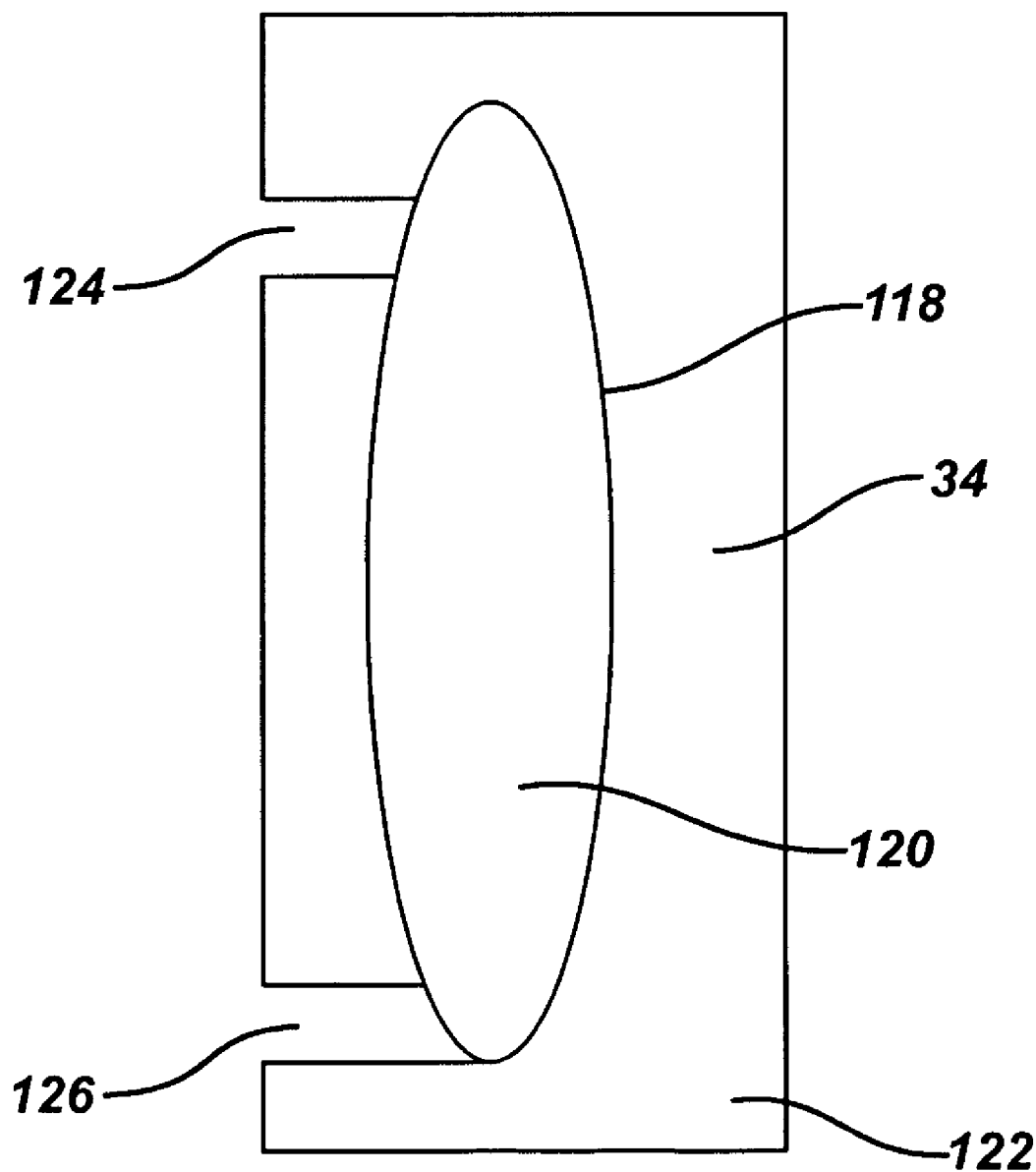
FIG. 10 is a cross sectional view of the cassette showing a cell therein.

Turning also now to FIGS. 9 and 10, the cassette 34 comprises a plurality of cells 118 containing liquid sterilant 120. Various structures of a cassette may be employed. The cassette 34 shown comprises a hard outer shell 122, preferably formed of an injection molded polymer, such as high impact polystyrene, high density polyethylene or high density polypropylene, which encloses the individual cells 118, the cells 118 being formed of a blow molded polymer such as low density polyethylene. However, a more rigid material can be used to form the cassette cells 118 in which case the outer shell 122 could be omitted. In the cassette 34 shown, an upper aperture 124 and lower aperture 126 through the shell 122 allows the upper and lower needles 70 and 72 to penetrate the shell. The cell 118 is formed of a material easily penetrated by the needles. If the cell 118 is formed of a more substantial material, a thinning of the material could be provided at the locations to be penetrated by the needles 70 and 72.

Figure 8:
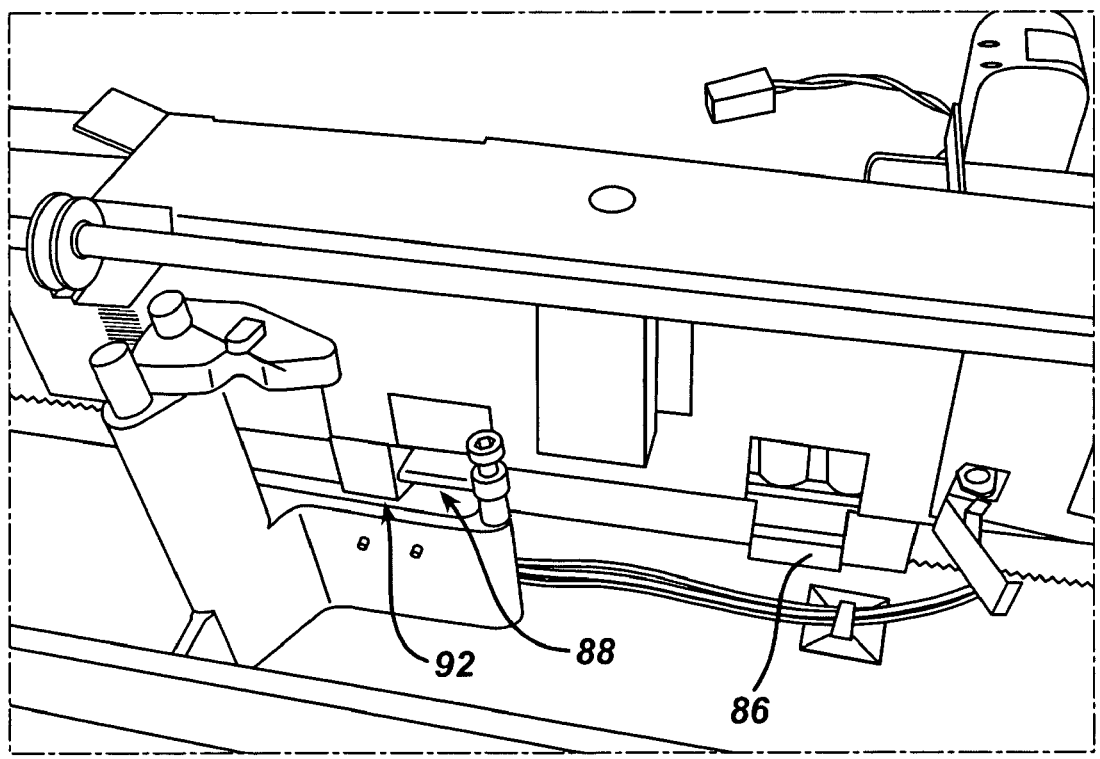
FIG. 8 is a rear perspective view of the cassette handling system of FIG. 2 showing its carriage in the home position.
Figure 11:
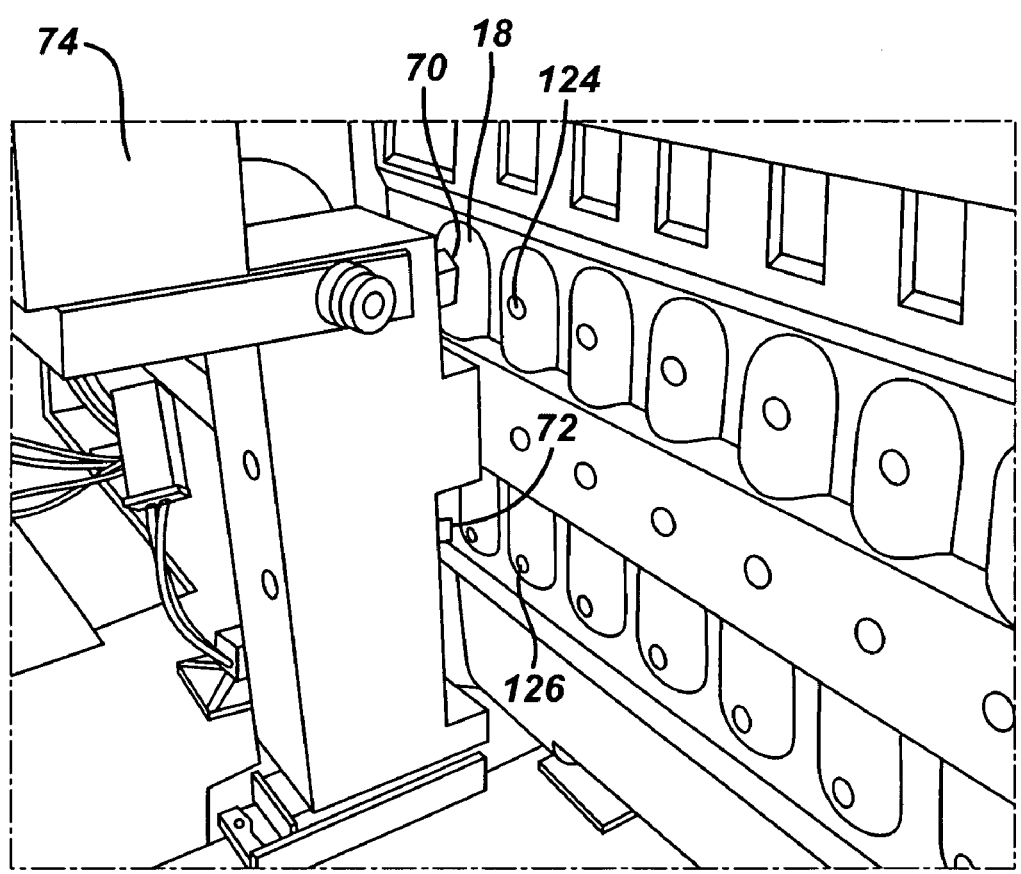
FIG. 11 is a front perspective view of the cassette handling system of FIG. 2 showing upper and lower needles on an extractor subsystem penetrating the first cell of the cassette.

The control system 28 uses the home position of FIG. 8 as a reference position for positioning the various cells 118 in front of the extractor subsystem 40. By moving the carriage 32 a predetermined amount from the home position a given cell 118 can be brought to face the extractor system 40. In FIG. 9, cell one has been placed in front of the extractor system 40. Turning also now to FIG. 11, an actuator 128 drives the extractor subsystem 40 toward the cassette 34 causing the upper and lower needles 70 and 72 to penetrate the upper and lower apertures 124 and 126 and enter the cell 118. After the needles have fully extended, the air pump 74 drives air into the cell 118 through the upper needle 70. The system waits a couple of seconds before starting the air pump 74 and opening the valve 76 to ensure proper placement and settling of the needles within the cell 118. The sterilant 120 flows out through the lower needle 72 and is piped off to the vaporizer 18. After a sufficient time to extract the sterilant 120, the air pump 74 switches off and the actuator retracts the extractor subsystem 40 from the cassette 34.

The vaporizer 18 connects to the vacuum chamber 14 which allows the lower needle 72 to easily be placed at a pressure below atmospheric. Thus, the pump 74 can optionally be replaced by a valve (not shown) open to atmosphere, in which case the incoming atmospheric pressure air will provide the driving force to empty the cell 118.

Rather than employ upper and lower needles 70 and 72, one needle having two lumens therethrough would suffice. One of the lumens would provide pressurizing gas and one would extract liquid sterilant. A further alternative arrangement would be to pierce the cell 118 vertically, or substantially so, from an upper part of the cell 118, preferably with such a double lumen needle. This would minimize leakage around the hole created by the needle entering the cell 118. Such entry would also allow the tip of the needle to come closer to the lowest point of the cell 118 for maximum extraction efficiency. If one desired to extract less than all of the contents of the cell 118, one method would be to position the needle extracting the sterilant, such as the lower needle 72 or the just mentioned double lumen needle, at the level in the cell 118 down to which extraction is desired. Liquid sterilant above the position would be extracted and sterilant below would remain. This would be particularly convenient with the just mentioned vertically traveling needle.

Figure 12:
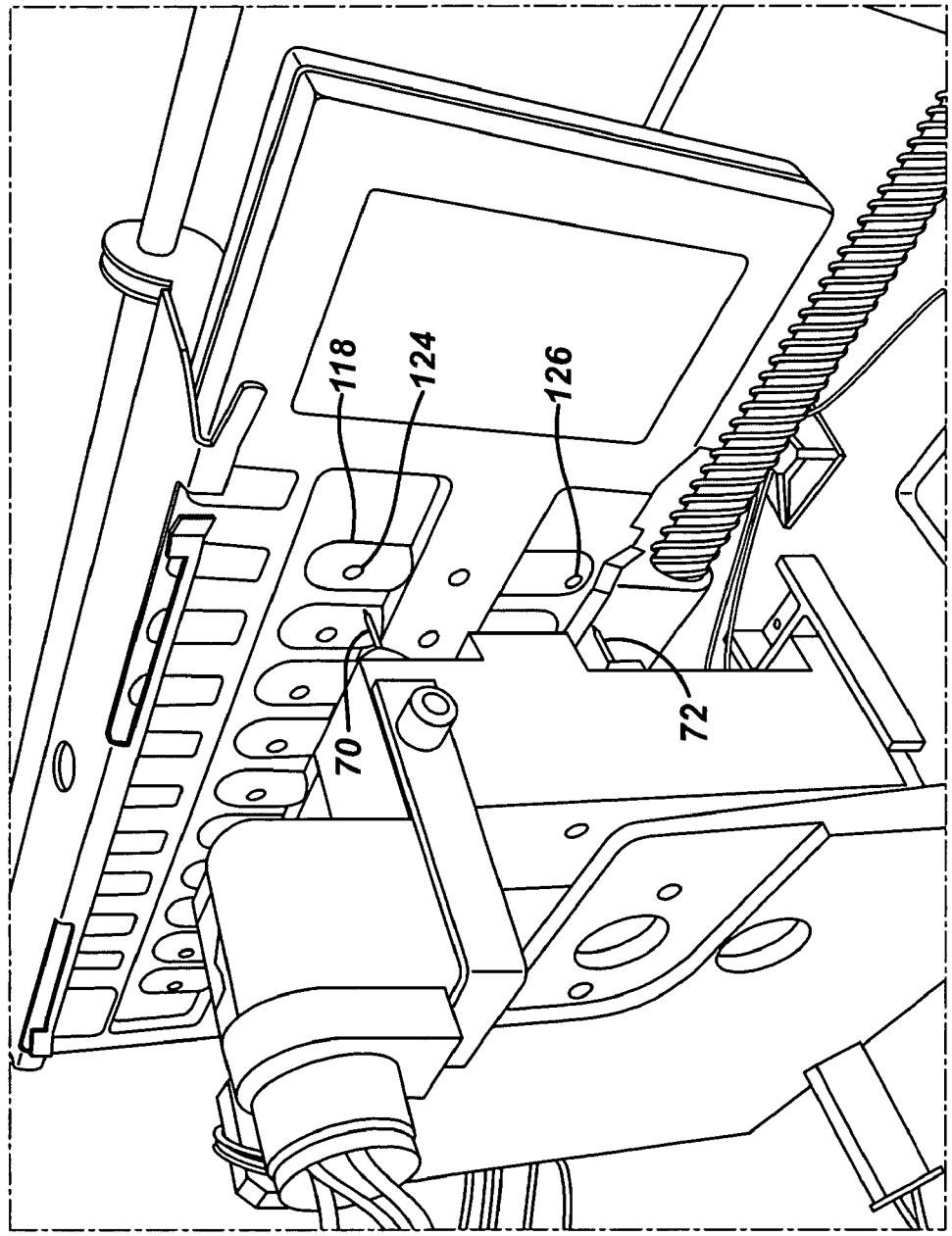
FIG. 12 is a front perspective view of the cassette handling system of FIG. 2 showing upper and lower needles on the extractor subsystem in position to penetrate the last cell of the cassette.
Figure 13:
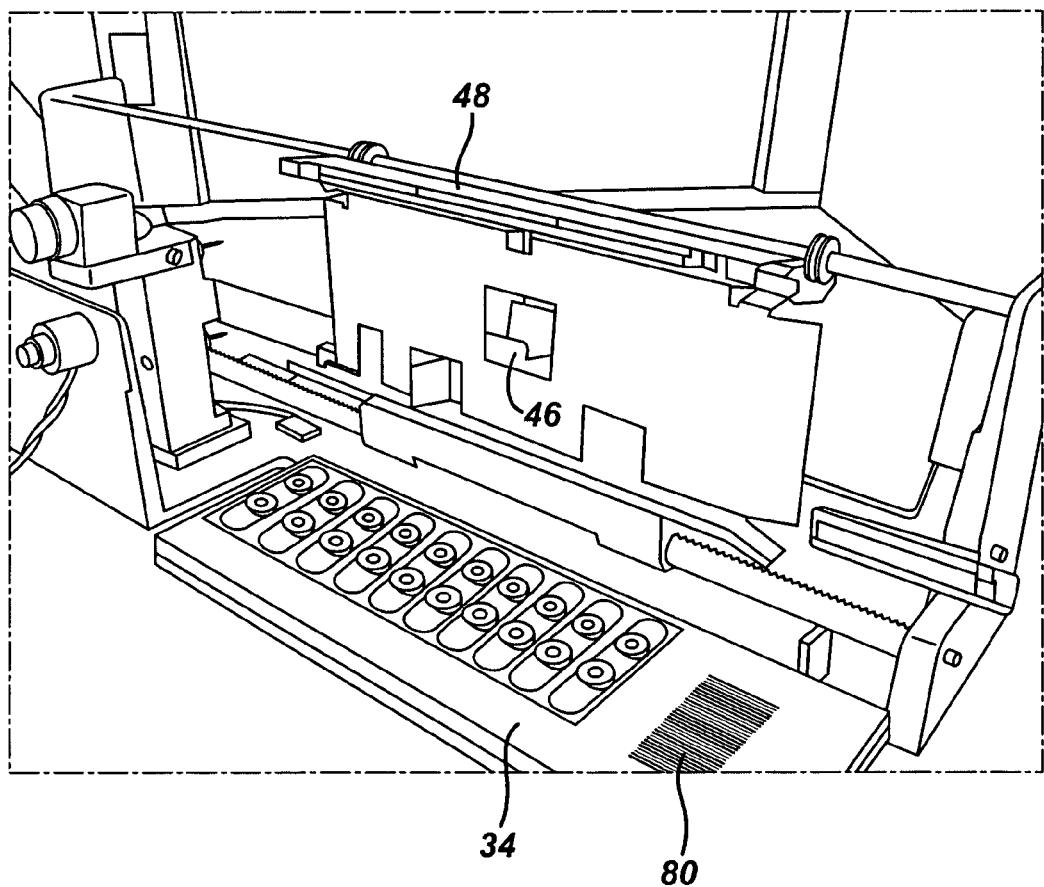
FIG. 13 is a front perspective view of the cassette handling system of FIG. 2 showing the cassette being ejected therefrom.

Turning also to FIG. 12, each time the control system 28 determines that a new dose of sterilant 120 is required, the stepper motor 38 moves the cassette to position the next cell 118 in front of the extractor subsystem 40 and a new extraction takes place. Multiple extractions may be employed for a given sterilization cycle. When the cassette 34 has been depleted, the carriage 32 moves towards the insert position thus causing the ejecting tab 98 to cam over the disposing cam 96 to rotate the top panel 48 upwardly and project the ejecting tab 98 through the opening 100 to drive the cassette 34 out of the carriage 32 as described above and as shown in FIG. 13. The cassette 34 falls into the spent cassette collection box 84 and the carriage 32 returns to the insertion position as shown in FIG. 5.

Figure 14:
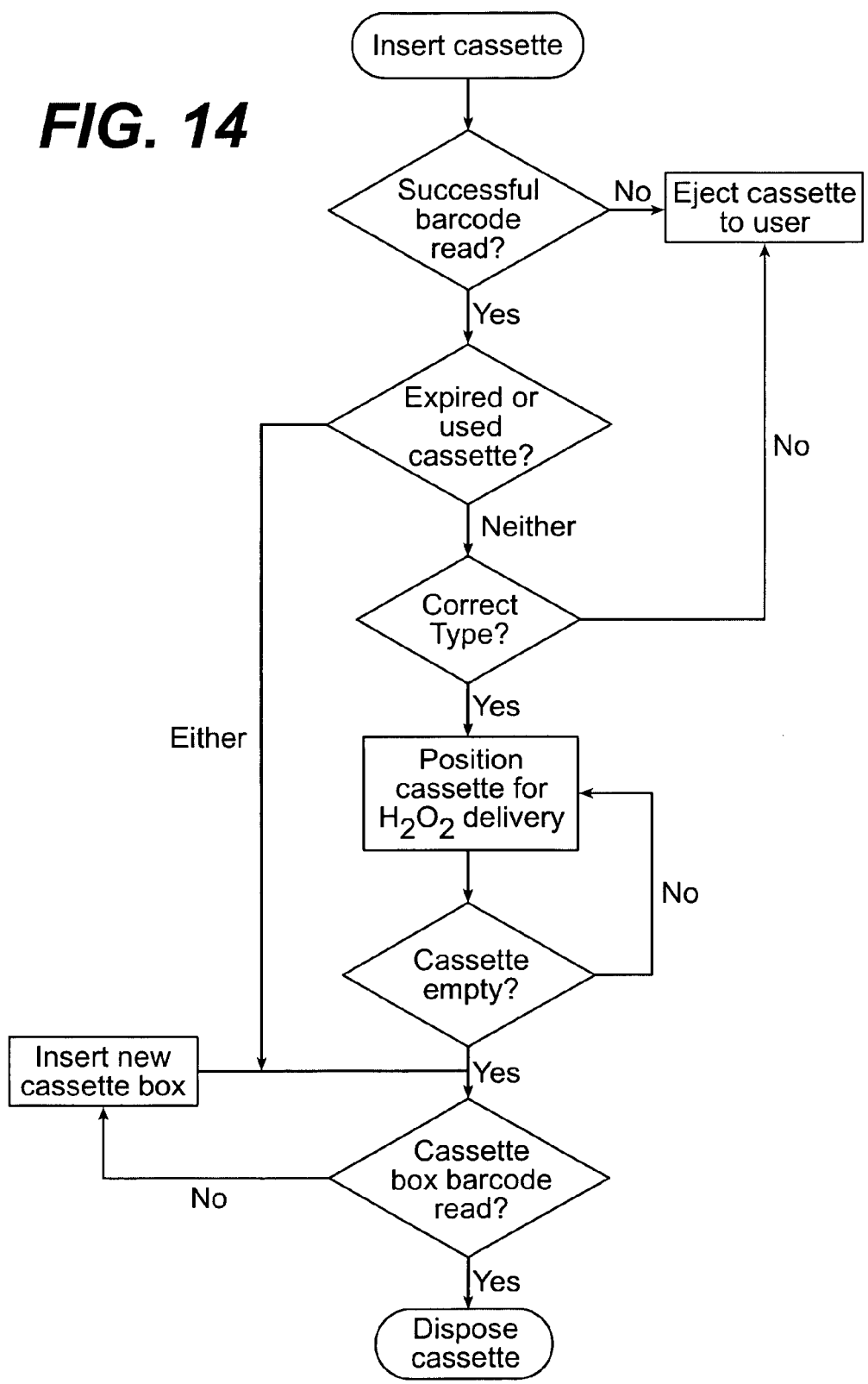
FIG. 14 is a flow chart of the cassette handling process.

The foregoing discussion described the operation of the cassette handling system in some detail. FIG. 14 shows, in block diagram form, the basic operation of the cassette handling system 12.

Figure 15:
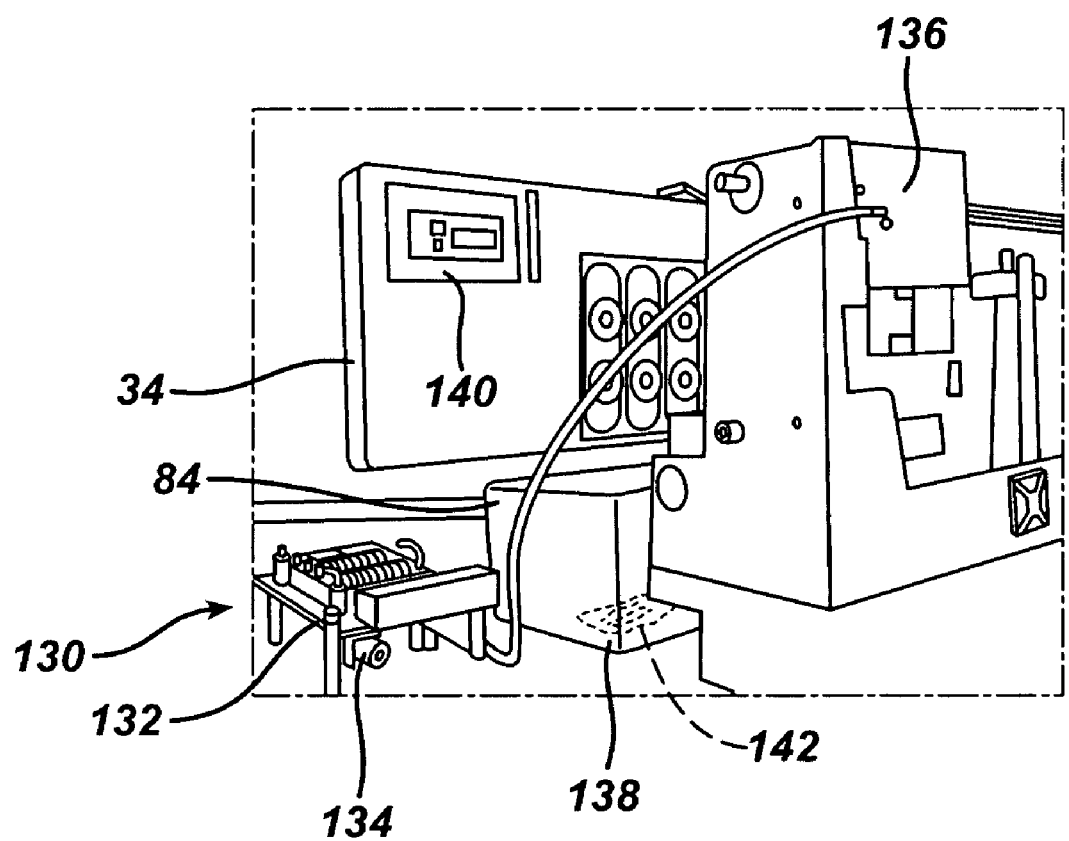
FIG. 15 is a rear perspective view of an alternative embodiment of a cassette handling system of the present invention employing RFID technology.

The system of reading barcodes on the cassette 34 and spent cassette box 84 can be replaced with radio frequency identification tags, commonly known as RFID tags. An RFID system 130 is shown in FIG. 15. It comprises a controller 132 connected via an SPDT reed relay 134 to a cassette insertion antenna 136 located on the carriage 32 and a cassette disposal antenna 138 located beneath the spend cassette box 84. Each cassette 34 carries a cassette RFID tag 140. Similarly, each spent cassette collection box 84 carries a collection box RFID tag 142. Preferably, the controller 132 comprises a Texas Instruments multifunction reader module S4100 and the RFID tags 140 and 42 comprise Texas Instruments RFID tag RI-101-112A each of which are available from Texas Instruments, Dallas, Tex.

The control system 28 (FIG. 1) selects one of the antennas, as for instance the cassette insertion antenna 136 and sends a signal to the relay 134 to engage this antenna with the RFID controller 132. The antenna reads the information stored on the cassette insertion RFID tag 140 which identifies the cassette 34 and its contents. The information read is similar to the information read using the barcode, however preferably, the RFID tag 140 has the ability to update the information stored thereon. Accordingly, additional data such as the filling status of individual cells 118 within the cassette 34 can be stored on the RFID tag. Thus, if the cassette 34 is removed and then reinserted into the sterilizer 10, or even into different sterilizer 10, the control system 28 can be apprised of the status of each of the individual cells 118 within the cassette 34. This allows the reuse of a partially used cassette 34. Also, since the RFID tag 140 can hold more data than the barcode 80, more data about the cassette 34, its contents and manufacturing can be included thereon.

The spent collection box antenna 138 reads the spent collection box RFID tag 142 to determine the presence or absence of the spent cassette collection box 84. Other data such as a unique identifier for the box 84, the capacity of the box 84, how many cassettes 34 are currently in the box 84 and how many of the cells 118 therein are not empty can be included on the RFID tag 142. The control system 28 can track how many cassettes 34 have been ejected into the box to determine whether it has room for more spent cassettes 34. The antenna 138 can also read the cassette RFID tags 140 and count the number of cassettes 34 within the box 84. When the box 84 is full the control system 28 alerts the operator, as by a message on a screen. This message can also include information regarding the cassettes 34 within the box 84. For instance if not all of the cassettes 34 have been completely drained the operator can be informed of this to decide if more careful disposal may be indicated.

RFID technology is disclosed in the following U.S. Patents, each of which is incorporated herein by reference: U.S. Pat. Nos. 6,600,420; 6,600,418; 5,378,880; 5,565,846; 5,347,280; 5,541,604; 4,442,507; 4,796,074; 5,095,362; 5,296,722; 5,407,851; 5,528,222; 5,550,547; 5,521,601; 5,682,143 and 5,625,341.

RFID tags typically comprise an antenna and an integrated circuit produced in a thin form factor so they can be inconspicuously placed upon an object such as the cassette 34. Radio frequency energy sent by the antennas 136 and 138 induce sufficient current within the antenna inside the RFID tags 140 and 142 to power the integrated circuit therein. Some types of RFID tags carry their own power source and have longer detection ranges, but that adds additional expense and is probably not justified for the present use.

Figure 16:
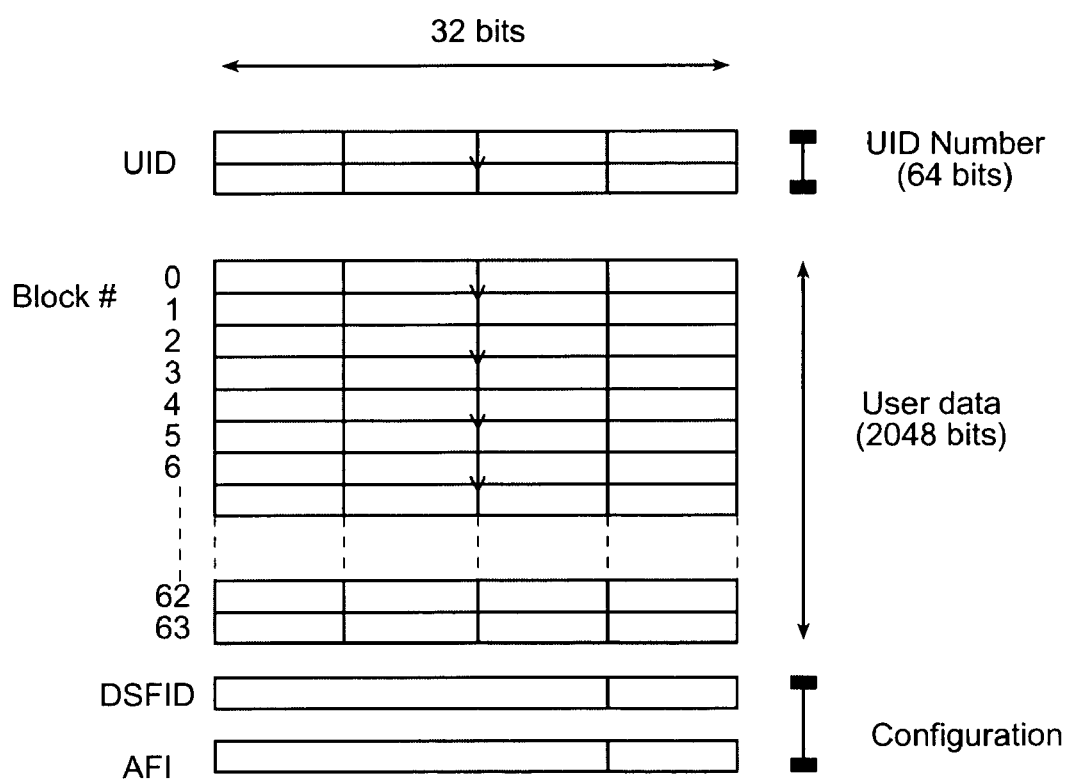
FIG. 16 is a memory map of an RFID tag of the cassette shown in FIG. 15.

FIG. 16 shows the memory map for the memory within the RFID tags 140 and 142. A 64-bit unique ID (UID) is set at the factory and cannot be changed. Each RFID tag has its own unique number here. Sixty-four 32-bit blocks can be programmed by the user. These can be populated with information such as the manufacture date, expiration date, product ID, serial number, lot numbers, manufacturing location, filling status of the cells, strength and type of sterilant, time spent within the sterilizer 10 and the like.

Some sterilants are affected by heat. The RFID tag 140 can optionally include temperature collection instrumentation and update that information on the tag. If design temperature profiles are exceeded, such as a maximum temperature or excessive temperature over a time period, then the cassette 34 can be rejected by the control system 28. Temperature measuring RFID tags are available from KSW-Microtec, Dreseden, Germany and from Identec Solutions, Inc., Kelowna, British Columbia, Canada. The interior of the sterilizer 10 where the cassette 34 sits may be higher than ambient temperature. Thus, it may be beneficial to put a maximum residence time (on board shelf life) on the tag 140 or even to update on the tag 140 this time the cassette has already spent inside of the sterilizer.

To test sterilant measuring equipment in the sterilizer 10, it may be beneficial to provide cassettes 34 having water or other fluids within one or more cells 118. Information regarding the special nature of the cassette 34 and its contents could be written onto the RFID tag.

During a cycle the sterilizer may only require part of the contents of a cell 118. For instance, a particular cycle may call for the contents of one and a half cells. The half filled nature of the cell 118 can be stored and then for the next cycle that cell 118 can be drained.

Preferably, communications between the tag 140 and 142 and the controller 132 are encrypted. For instance, the UID can be XORed with an eight-bit master key to form a diversified key for encrypting the data. Encryption algorithms such as the data encryption standard (DES) triple DES, asymmetrical encryption standard (AES) or RSA security can be used for the encryption. The RFID controller 132 reads the data and the algorithm in the control system 28 decrypts the data to reveal the stored information.

Other methods could be used to communicate between the cassette 34 and the sterilizer 10. For instance information could be stored magnetically on the cassette 34, such as with a magnetic encoded strip, and be read by a magnetic reader on the sterilizer. Wireless technology is becoming cheaper every day and it is envisioned that the cassette 34 could include an active transmitter and a power source (i.e. a battery) such as powered RFID tags or Bluetooth, 802.11b or other communication standard.

Further, the sterilizer 10 can be set up to communicate back to a central source, such as the manufacturer or distributor thereof, and provide information regarding its performance and the performance of the cassettes 34. Poorly performing cassettes 34 could be identified, as for instance sterilant monitors in the sterilizer not detecting sterilant during a cycle thus indicating some failure such as an empty cassette or bad sterilant therein. An improperly manufactured batch of cassettes 34 could then be quickly identified and recalled. Such communication could occur over telephone, pager or wireless telephone networks or over the Internet.

Figure 17:
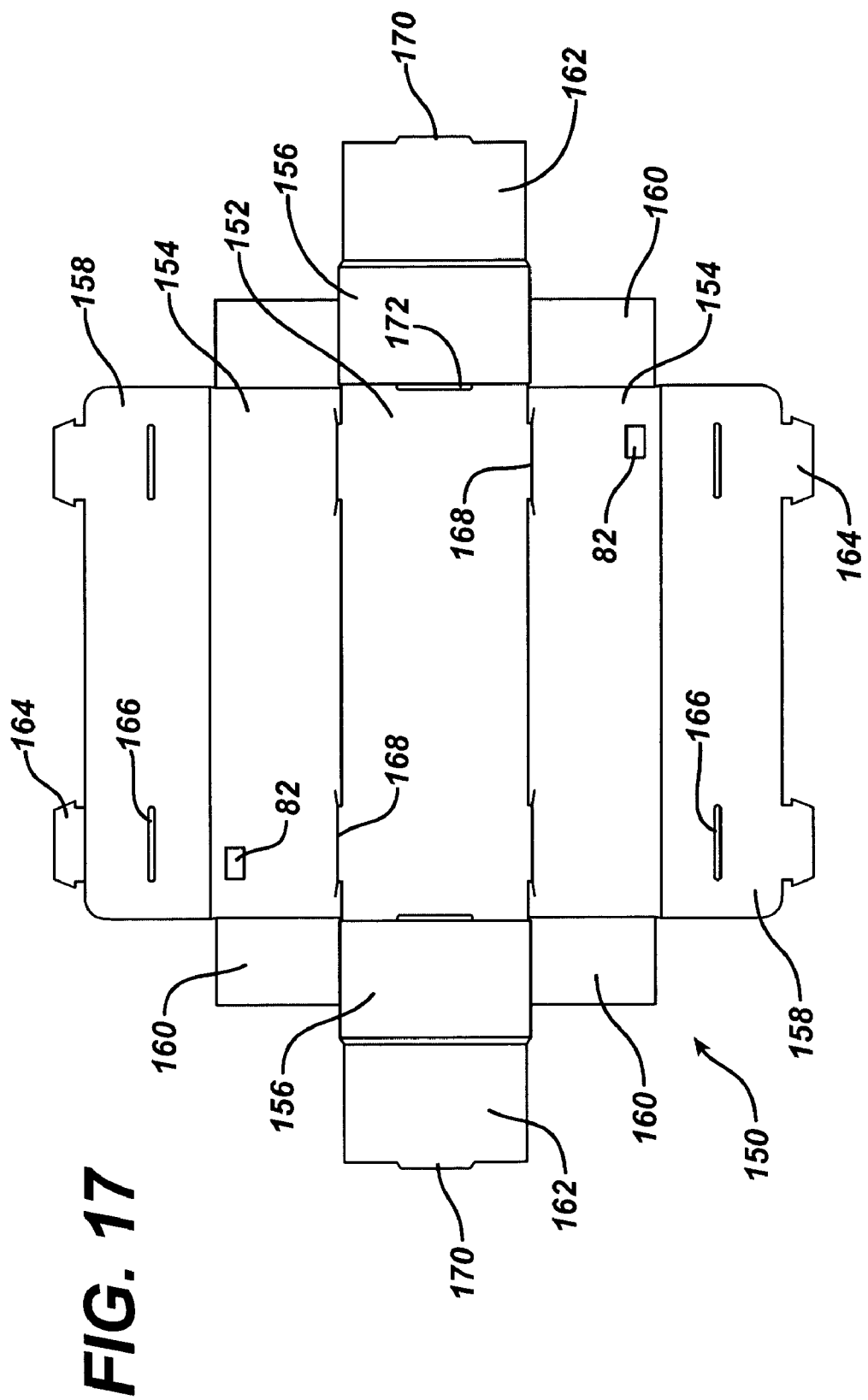
FIG. 17 is a top plan view of an unfolded blank for forming the spent cassette collection box of FIG. 4.
Figure 18:
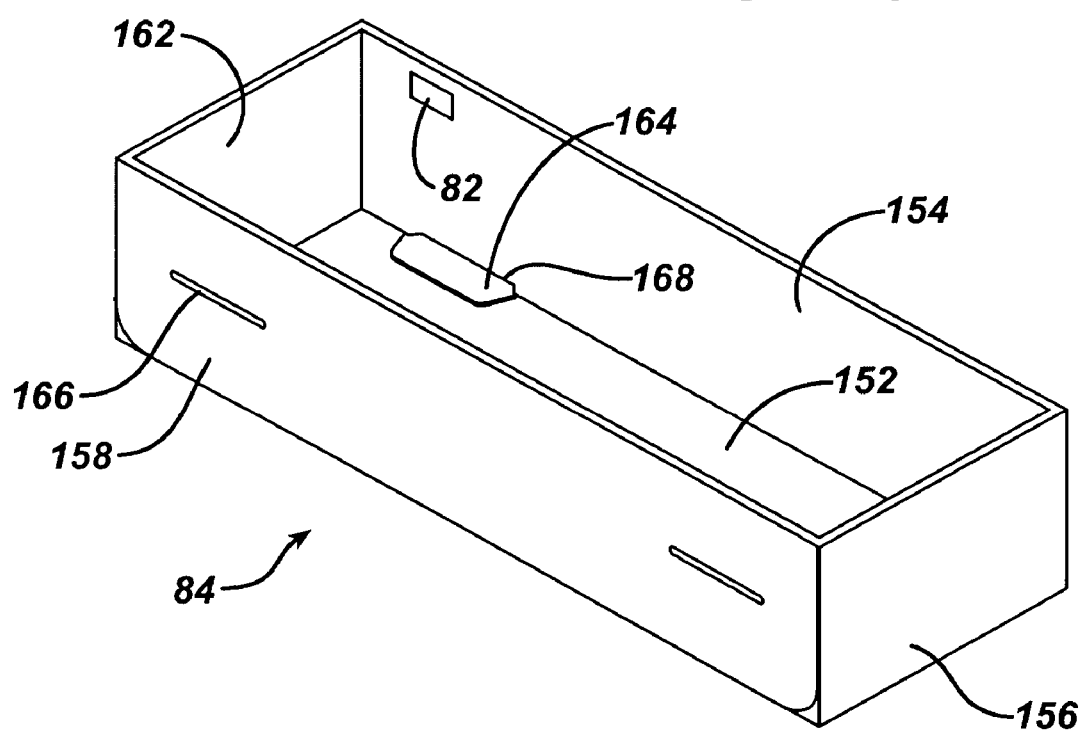
FIG. 18 is a perspective view of the blank of FIG. 17 folded to form the spent cassette collection box.

Turning now also to FIGS. 17 and 18, the spent cassette collection box 84 is preferably folded from a single sheet of printed cardboard or other stock. FIG. 17 shows an unfolded blank 150 and FIG. 18 shows the blank 150 folded to form the spent cassette collection box 84.

The blank 150 is divided by a series of fold lines (shown dashed) and cut lines into a bottom panel 152, side panels 154, end panels 156 and top flaps 158. Folding tabs 160 extend laterally from the side panels 154. Additional folding tabs 162 extend laterally from the end panels 156. Barcodes 82 are printed on the side panels 154 in a position to be visible in an upper interior corner of the spent cassette collection box 84 when it is folded into the configuration shown in FIG. 18. A pair of top flap locking tabs 164 extend from the top flaps 158 and fit into slots 166 in the opposing top flap 158 when the box 84 is closed and into slots 168 at the intersection of the bottom panel 152 and side panel 154 when the box 84 is opened.

To fold the box, the folding tabs 160 on the side panels 154 are folded upwardly and then the side panels 154 are folded upwardly, thereby aligning the folding tabs 160 with the intersection between the bottom panel 152 and the end panels 156. The end panels 156 are then folded upwardly and the end panel folding tabs 162 are folded downwardly over the folding tabs 160. Locking tabs 170 on the end panel folding tabs 162 fit into slots 172 at the intersection between the bottom panel 152 and end panels 156.

To place the box 84 into the open position as shown in FIG. 18, the top flaps 158 are folded downwardly to the outside and the locking tabs 164 fitted into the slots 168. Once the box 84 is filled with spent cassettes, the top flaps 158 are folded upwardly over the top and the locking tabs 164 can then be fitted into the slots 166 on the opposing top flaps 158. This unique folding arrangement allows spent cassettes 34 to fall into the open box 84 easily without the top flaps 158 getting in the way and also allows easy closure of the box 84 once it has become filled.

While the invention has been particularly described in connection with specific embodiments thereof, it is to be understood that this is by way of illustration and not of limitation, and that the scope of the appended claims should be construed as broadly as the prior art will permit.

What is claimed is:

1. A method for tracking a sterilant cassette within a sterilizer comprising the steps of:
   reading for a presence of the cassette within a cassette processing area of the sterilizer by transmitting a non-optical electromagnetic signal between the cassette and a receiver on the sterilizer;
   via the electromagnetic signal transmitting identifying information between the cassette and the receiver, wherein the identifying information comprises an expiration date;
   verifying that a proper cassette is loaded into the sterilizer based upon the identifying information, wherein verifying that a proper cassette is loaded includes determining if the expiration date has passed; and
   rejecting the cassette if the expiration date has passed.

2. A method according to claim 1 wherein the electromagnetic signal comprises a magnetic coupling between the receiver and the cassette.

3. A method according to claim 1 wherein the electromagnetic signal comprises an inductive coupling between the receiver and the cassette.

4. A method according to claim 1 wherein the electromagnetic signal comprises a conductive coupling between the receiver and the cassette.

5. A method according to claim 1 wherein the electromagnetic signal comprises a radio frequency transmission.

6. A method according to claim 5 wherein the receiver comprises one or more antennas.

7. A method according to claim 6 comprising the step of sequencing use of the antennas by the receiver to identify a location of the cassette.

8. A method according to claim 1 wherein the cassette comprises an RFID tag for storing data, the stored data comprising the identifying information.

9. A method according to claim 8 comprising the step of altering a portion of the data stored in the RFID tag.

10. A method according to claim 9 wherein the data stored on the RFID tag comprises a filling status of a sterilant in the cassette, and wherein the method comprises the step of updating the filling status data as the sterilant is removed from the cassette.

11. A method according to claim 10 wherein the cassette comprises a plurality of cells containing the sterilant, wherein the RFID tag comprises a filling status of the sterilant in each of the cells, and wherein the method comprises the step of updating the filling status data for a cell as the sterilant is removed from that cell.

12. A method according to claim 11 comprising the steps of draining less than all of the contents of one of the cells and storing this information on the RFID tag.

13. A method according to claim 8 wherein the data stored on the RFID tag comprises temperature information regarding the shipping and storage temperatures to which the cassette has been subjected, and wherein the method comprises removing a quantity of the sterilant from the cassette based on the temperature information.

14. A method according to claim 9 wherein the RFID tag comprises temperature sensing instrumentation and the stored data comprises temperature information regarding the shipping and storage temperatures to which the cassette has been subjected.

15. A method according to claim 14 comprising removing a quantity of the sterilant from the cassette based on the temperature information.

16. A method according to claim 9 comprising updating the stored data with one or more cycle parameters.

17. A method according to claim 16 comprising updating the stored data with a concentration of sterilant achieved during a cycle.

18. A method according to claim 16 comprising querying the updated data to monitor cycle performance.

19. A method according to claim 9 comprising updating the stored data with an amount of the time the cassette has spent within the sterilizer.

20. A method according to claim 1 comprising the step of reading a presence and a filling status of a spent cassette collection box via a non-optical electromagnetic signal.

21. A method for tracking a sterilant cassette within a sterilizer comprising the steps of:
   exchanging information between the cassette and a receiver on the sterilizer via a non-optical electromagnetic signal, wherein the cassette comprises a plurality of cells containing a sterilant; and
   rejecting the cassette if an expiration date of the cassette has passed, wherein the exchanged information comprises the expiration date and at least one of:
   a sterilization cycle parameter;
   a concentration of sterilant achieved during a sterilization cycle; and
   a type of cycle for which one or more of the cells is intended.

22. A method according to claim 21, comprising the steps of:
   determining the presence of a spent cassette collection box via a non-optical electromagnetic signal; and
   determining a filling status of the spent cassette collection box.

* * * * *

UNITED STATES PATENT AND TRADEMARK OFFICE
CERTIFICATE OF CORRECTION

PATENT NO. : 7,602,284 B2
APPLICATION NO. : 10/793115
DATED : October 13, 2009
INVENTOR(S) : Wong et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 571 days.

Signed and Sealed this

Fourteenth Day of December, 2010

David J. Kappos
*Director of the United States Patent and Trademark Office*